United States Patent [19]

Fearing

[11] 4,199,534
[45] Apr. 22, 1980

[54] POLY (OXYORGANOPHOSPHATE/PHOSPHONATE) AND PROCESS FOR PREPARING

[75] Inventor: Ralph B. Fearing, Bardonia, N.Y.

[73] Assignee: Stauffer Chemical Company, Westport, Conn.

[21] Appl. No.: 898,241

[22] Filed: Apr. 20, 1978

[51] Int. Cl.$^2$ ............................................. C07F 9/09
[52] U.S. Cl. .................................... 260/928; 260/978; 521/169; 8/115.5
[58] Field of Search ............................. 260/928, 978

[56] References Cited

U.S. PATENT DOCUMENTS

| | | | |
|---|---|---|---|
| 3,099,676 | 7/1963 | Lantham | 260/928 |
| 3,639,545 | 2/1972 | Wilcox | 260/971 |
| 3,767,732 | 10/1973 | Klose | 260/928 |
| 3,850,859 | 11/1974 | Wormann et al. | 260/2.5 AJ |
| 3,855,359 | 12/1974 | Weil | 260/928 |
| 3,891,727 | 6/1975 | Weil | 260/928 |

FOREIGN PATENT DOCUMENTS

1468053  3/1977  United Kingdom ..................... 260/928

OTHER PUBLICATIONS

Schep et al., "Joernaal van due Suid-Afrikaanse Chemises Instituut", Band XXVII, 1974, pp. 63-69.

Primary Examiner—Anton H. Sutto
Attorney, Agent, or Firm—Roger S. Benjamin

[57] ABSTRACT

Phosphorus containing flame retardants are prepared by a two step process having as essential steps:
  (1) reacting diorgano organophosphonate with reactant comprising phosphorus oxide reagent to yield a metaphosphate/phosphonate reaction product, and thereafter;
  (2) reacting the reaction product of step (1) with reactant comprising epoxide to yield poly (oxyorganophosphate/phosphonate) product.

Selected poly (oxyorganophosphate/phosphonate) products contain a backbone structure of repeating units represented by the average formula:

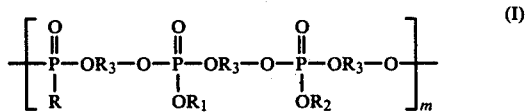

wherein m is an integer from 1 to 50; R, $R_1$, and $R_2$ are individually selected from saturated hydrocarbon radical, alkaryl radical, aralkyl radical, and aryl radical; and $R_3$ is:

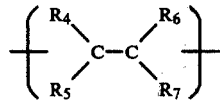

wherein $R_4$, $R_5$, $R_6$, and $R_7$ are individually selected from hydrogen atom, hydrocarbon radical, and halogenated hydrocarbon radical.

Articles and compositions such as textiles and polyurethanes are rendered flame retardant by incorporation of poly (oxyorganophosphate/phosphonate) products of Formula (I).

19 Claims, No Drawings

POLY (OXYORGANOPHOSPHATE/PHOSPHONATE) AND PROCESS FOR PREPARING

BACKGROUND OF THE INVENTION

Poly(methylphosphate/phosphonate) products have been prepared by the reaction of phosphorus pentoxide with trimethyl phosphate or dimethyl methylphosphonate. The statistical distribution, nuclear magnetic resonance characteristics, and other non-chemical features of phosphate and phosphonate groups in such products are described by R. A. Schep, J. H. H. Coetzee, and S. Norval, THE POLYMER PRODUCTS FORMED WHEN DIMETHYL METHYLPHOSPHONATE REACTS WITH PHOSPHORUS PENTOXIDE, Joernaal Van Die SuidAfrikaanse Chemises Instituut. Band XXVII, 1974, pages 63 to 69.

U.S. Pat. No. 3,099,676 (to W. M. Lanham, patented July 30, 1963) described polyphosphates produced by the reaction of vicinal epoxides with pyrophosphoric acids. Lanham prepares heavily hydroxylated derivatives of pyrophosphoric acid (two phosphorus atoms). An epoxide residue is inserted into the —P(O)—O—P(O)— portion of the acid.

U.S. Pat. No. 3,639,545 (to R. D. Wilcox, patented Feb. 1, 1972) describes the reaction of a bisalkylene pyrophosphate with vicinal alkylene oxide to form a cyclic alkylene phosphate alkylene ester of the formula:

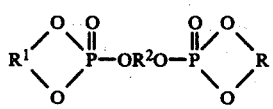

Wilcox prepares products having terminal alkylene groups and an epoxide residue inserted into the phosphorus anhydride structure. The Wilcox products contain two phosphorus atoms.

U.S. Pat. Nos. 3,767,732 (to W. Klose) and 3,850,859 (to J. Wortmann, et al.) describe halogenated phosphorus containing polyols of the general formula:

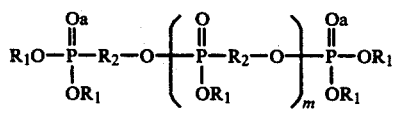

The Klose and Wortmann patents describe compounds having two to six phosphorus atoms in repeating linkages of —P(O)—OR—O—. Each phosphorus atom has a pendant oxyorgano group containing hydroxyl functionality.

U.S. Pat. No. 3,855,359 (to E. D. Weil, patented Dec. 17, 1974) describes copolycondensed vinylphosphonate flame retardants containing as a portion of the repeating units:

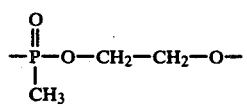

U.S. Pat. No. 3,891,727 (to E. D. Weil, patented June 24, 1975) describes fire retardant phosphorus oligomers formed by condensation of beta-haloalkyl esters of pentavalent phosphorus acid. These oligomers may contain repeating units of the general formula:

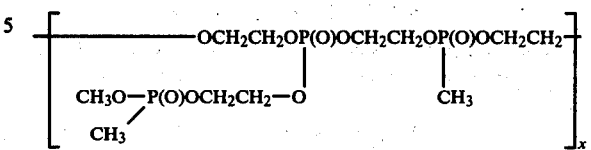

British Patent No. 1,468,053 (to Stauffer Chemical Co.) describes the condensation of a beta-haloalkylphosphate and a dialkyl phosphonate to yield a halogen free condensation product illustrated by the formula:

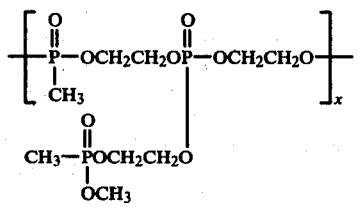

The Weil patents and British Pat. No. 1,468,053 describe phosphorus based flame retardants having a —P—(O)—OR—O— backbone formed from condensation-type reactions. Vinyl, haloalkoxy, or organophosphorus groups pendant from backbone phosphorus atoms are a required feature of structure. The condensation-type reactions do not incorporate all of the starting reactants into the final product. Organic compounds split out during the course of the reaction necessitate purification or byproduct recovery steps.

The condensation-type reactions are preferably conducted at above ambient temperatures. Since these reactions are endothermic energy must be added to the reaction system.

THE INVENTION

This invention is a process for making poly (oxyorganophosphate/phosphonate) flame retardants. Novel poly (oxyorganophosphate/phosphonate) products produced by the process of this invention are also disclosed.

Another aspect of this invention is a flame retardant polyurethane composition containing the poly (oxyorganophosphate/phosphonate) products of this invention.

Still another aspect of this invention is a textile made flame retardant by combination with the poly (oxyorganophosphate/phosphonate) products of this invention.

DETAILED DESCRIPTION OF THE INVENTION

The poly (oxyorganophosphate/phosphonate) flame retardants are prepared by a two step process. In the first step diorgano organophosphonate is reacted with phosphorus oxide reactant. In the second step the first step reaction product is reacted with epoxide alone or epoxide and an alcohol. The final product described herein as poly (oxyorganophosphate/phosphonate) has a structure which is not completely understood. NMR examination of poly (oxyethylene methylphosphate/methylphosphonate) prepared according to the method of this invention discloses a structure more linear than analogous polymers produced by condensation-type synthesis routes.

FIRST PROCESS STEP

The first of two process steps is the reaction of diorgano organophosphonate with phosphorus oxide reagent.

Suitable diorgano organophosphonate reactants are represented by the formula:

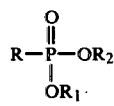

wherein R, $R_1$, and $R_2$ are the same or different organoradicals. Suitable organo-radicals may be divided into two groups. Group I are organo radical found pendant from backbone phosphorus atoms in some prior art condensation-type reaction products and include; alkylene radicals, halogenated hydrocarbon radicals, organophosphorus radicals, or organo-nitrogen radicals. Specific organo-phosphonates include 2-chloroethyl vinylphosphonate, diethyl polybromobiphenyl phosphonate, dimethyl cyanoethyl phosphonate, polycondensed 2-chloroethyl phosphonate oligomers such as those disclosed in U.S. Pat. No. 3,014,956, 2-chloroisopropyl phosphonate, 2-bromo isopropylphosphonate, and bis-2-chloroethyl chloroethylphosphonate.

Group II phosphonate organo-radicals used in preparing preferred flame retardants according to this invention include saturated hydrocarbon radicals, alkaryl radicals, aralkyl radicals and aryl radicals. Particularly preferred are organo phosphonates where R, $R_1$, and $R_2$ are alkyl radicals of one to ten carbon atoms. Specific phosphonate reactants corresponding to the Group II radicals include dimethyl methylphosphonate, diethyl methylphosphonate, dimethyl ethylphosphonate, diethyl ethylphosphonate, methyl ethyl propylphosphonate, and diethyl phenylphosphonate. Especially preferred as reactants are dimethyl methylphosphonate, diethyl ethylphosphonate or diethyl methylphosphonate.

Mixtures of diorgano organophosphonates from among the phosphonates of Groups I and II may be used.

The phosphorus oxide reagent may be a phosphorus anhydride-acid, or oxide. Phosphorus pentoxide is the essential phosphorus oxide reactant used in the process of this invention. Minor portions of phosphorus acids may be tolerated with the phosphorus pentoxide but the acid will serve to break the polymer chain and does not positively assist in the essential first step reaction of this invention.

The relative proportions of reactants expressed as the mole ratio of diorgano organophosphonate to $P_2O_5$ is generally in the range between 1:1 to not more than 2.5:1. Consequently, in the repeating unit of Formula (I), the mole ratio of organophosphonate phosphorus to phosphate phosphorus can range from 0.5 to 1.25. The choice of reactant proportions is one method of adjusting the degree of polymerization of the first step reaction product. Low ratios tend to give high molecular weight, highly viscous products. With mole ratios of diorgano organophosphonate to $P_2O_5$ greater than 1:1, the diorgano organophosphonate acts as a chain terminating agent and lowers the degree of polymerization in the product. The minimum average of phosphorus atoms desired in the first step reaction product is three, but there is no upper limit except for practical considerations of viscosity and product handling. Preferred mole ratios are in the range of 1.05:1 to 2.25:1.

Another method of adjusting the degree of polymerization of the first step reaction product is to introduce an alcohol into the reaction system. Alcohol acts to sever the meta-ester reaction product to give a structure of lower molecular weight. The alcohol reaction is illustrated by the following equation:

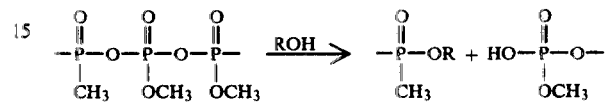

Alcohol may be added during or after the reaction of diorgano organophosphonate and $P_2O_5$.

Alcohol should not be used in proportions of more than one mole of hydroxyl per three moles of phosphorus anhydride unit in the polymer chain to maintain a minimum average chain containing three phosphorus atoms in the final product.

The choice of alcohol optionally employed in the first reaction step is not critical. Alcohol used in the first step process may be selected from the range of alcohols suitable for use in the second process step; notwithstanding that alcohols are employed in the first and second steps of this invention for different purposes.

The reaction is exothermic so that controlled addition of at least one reactant is preferred. Reaction temperature is not critical, but is generally between the limits of 0° C. to 200° C., with limits of 15° C. to 85° C. being preferred.

The first step reaction product contains a —P(O)—O—P(O)— backbone and is typically in the form of a viscous liquid. It is generally unnecessary to purify the first step reaction product for use in the reactions of the second process step.

SECOND PROCESS STEP

The second process step is the reaction of metaphosphate/phosphonate ester with a strained-ring oxygen heterocycle reactant such as an oxetane or epoxide. Optionally, the first step reaction product may be reacted with both an alcohol and an epoxide to yield substituted polyesters of phosphorus.

Epoxides are preferred oxygen heterocycle compounds for reactants. The choice of oxygen heterocycle reactant is not critical. Illustrative of suitable oxygen heterocycle compounds are epoxides represented by the formula:

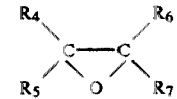

wherein $R_4$, $R_5$, $R_6$, and $R_7$ individually can be hydrogen atom or radicals selected from the group alkyl, aryl, or haloalkyl. Specific epoxides or classes of epoxides useful in the practice of this invention are ethylene oxide; 1,2-epoxypropane, epoxybutanes, epoxyhexanes, epichlorohydrin, epibromohydrin, and styrene oxide. A mixture of epoxides may be used.

Epoxides are believed to add into portions of the metaphosphate/phosphonate ester first step reaction product at points of structure such as:

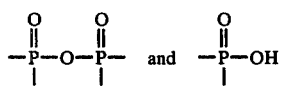 (II)

to give poly (oxyorganophosphate/phosphonate) structures such as:

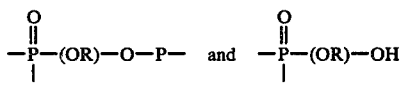

The second step reaction may be conducted using as reactants only epoxide and metaphosphate/phosphonate ester. Typically, epoxide is used in proportions of from 0.8 to 1.3 moles per gram atom of phosphorus in the metaphosphate/phosphonate ester product. The upper limit of epoxide addition depends only on the number and proportion of formulae (II) groups in the first step reaction product.

Hydroxyl-bearing compounds such as water or alcohols may be advantageously added to the reaction system of the second step to modify the structure of the final product. Metaphosphate/phosphonates are readily alcoholized to give reaction products having increased hydroxyl functionality and decreased molecular weight. Other desirable terminal group features may be derived from the alcohol structure, for example, branched carbon chains or halogen content. Illustrative alcohol reactants are shown in the following formulae:

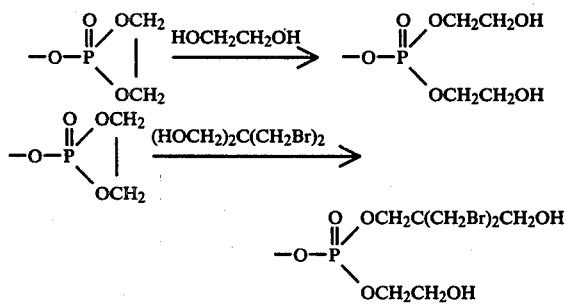

A wide variety of alcohols have utility in the second reaction step. Suitable classes of alcohols include primary alcohols, secondary alcohols, tertiary alcohols, phenols, aromatic alcohols, polyhydric alcohols, alcohol acids, alcohol esters, alcohol amides, alcohol ethers, sulfur-containing alcohols, phosphorus-containing alcohols, halogenated alcohols, and oxyorgano (halo) phenols. A mixture of alcohols may be used.

Examples of specific alcohols useful in the practice of this invention are methanol, ethanol, isopropanol, secondary butyl alcohol, benzyl alcohol, phenol, ethylene glycol, glycerol, glycolamide, ethanolamine, dibromopropanol, dibromonoeopentylene glycol, oxyethylated tetrabromo bisphenol A, pentaerythritol, and dimethyl hydroxymethyl phosphonate.

The use of alcohol to eliminate acidic structures is described in U.S. Pat. No. 3,891,727 the content of which is incorporated herein by reference.

In the second step reaction alcohol may be used after reaction with the epoxide is completed. Alternatively, a portion of epoxide sufficient to add into the major portion of phosphorus anhydride linkages of the product may first be reacted, then the resultant product reacted with alcohol, and the product thereafter treated with the balance of epoxide reactant.

The reaction may be conducted without a catalyst if a product containing a high proportion of cyclic ester groups is satisfactory. The use of a catalyst in the presence of an epoxide opens the cyclic esters and rejoins them into the poly (oxyorganophosphate/phosphonate) backbone. Use of catalyst also reduces the time and temperature required for practical reaction rates. Lewis acids and bases in amounts of from about 0.01 to about 10.0 weight percent are suitable catalysts for the practice of this invention. Illustrative catalysts include the following compounds:

| | |
|---|---|
| Aluminum Chloride | Butyl Lithium |
| Alkali Hydroxide | Alkali Phosphate |
| Tetra (Isopropyl) Titanate | Boron Trifluoride Etherate |
| Alkali Ethoxide | Boron Trifluoride |
| Stannous Octoate | Zinc Chloride |
| Magnesium Chloride | Antimony Trichloride |
| Titanium Tetrachloride | Sodium Borohydride |
| Sodium Methoxide | |

Reaction temperature for the second step is in the range of about 0° C. to about 180° C., with 40° C. to 60° C. being preferred. Reaction time for both the first and second steps can be from several minutes to several days. Pressure is not critical and both the first and second step reactions are generally conducted at atmospheric pressure. For selected reactants such as ethylene oxide the use of superatmospheric pressure has the advantage of liquifying all reactants.

Residual acidify in the second step reaction product can also be removed by posttreatment with alkylene oxides as taught in U.S. Pat. No. 3,959,415.

Unwanted color in the reaction product may be removed by inclusion of from about 0.01 to about 2.0 weight percent of an organo phosphite such as trimethyl phosphite in the reaction mixture. The progress of the reaction may be determined by withdrawing samples and monitoring properties such as viscosity, density or rate of reaction exotherm.

The step one and step two reactions are conducted in liquid phase using the reactants themselves as reaction medium. Inert compounds such as liquid aliphatic, aromatic or halogenated hydrocarbons may constitute the reaction medium.

At the conclusion of the reaction the poly (oxyorganophosphate/phosphonate) ester may be purified by a variety of procedures. By-products, inert reaction medium, and unreacted materials, if any, may be removed by procedures such as sparging, vacuum stripping, steam distillation, thermal fractionation, or solvent extraction.

The process of this invention may be carried out in conventional reaction vessels having inlets, outlets, material conveyancing means, and desirably provision for agitation and temperature and pressure adjustment.

The progress of the second step reaction sequence may be determined by analysis of acid number or monitoring by instrumental means such as NMR.

A preferred group of product prepared according to the process of this invention are the poly (oxyorganophosphate/phosphonate) products represented as repeating units having the average formula:

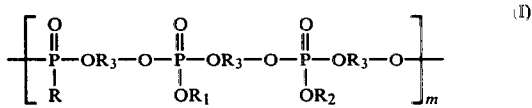

wherein m is an integer from 1 to 50; R, $R_1$ and $R_2$ are the same or different and are selected from saturated hydrocarbon radicals, alkaryl radicals, aralkyl radicals, and aryl radicals; and $R_3$ is:

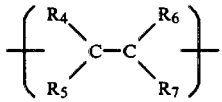

wherein $R_4$, $R_5$, $R_6$, and $R_7$ are individually selected from hydrogen atom, alkaryl radicals, aralkyl radicals, aryl radicals, saturated hydrocarbon radicals, and halogenated hydrocarbon radicals. The pendant groups —R, —$OR_1$, and —$OR_2$ shown in Formula (I) are believed to be statistically distributed in the polymeric reaction product with a mole ratio of —$OR_1$ plus $OR_2$ to —R groups of two to one. Preferred R, $R_1$, and $R_2$ groups are alkyl radicals of one to ten carbon atoms. For small values of m in the repeating unit of Formula (I), the mole ratio of organophosphonate phosphorus to phosphate phosphorus can be as high as 1.25. Preferred $R_4$, $R_5$, $R_6$, and $R_7$ groups are hydrogen atom and alkyl radicals of one to ten carbon atoms.

End groups for the poly (oxyorganophosphate/phosphonate) of Formula (I) are typlified by but not limited to the following:

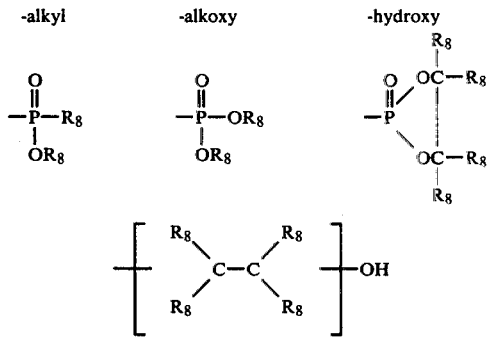

wherein $R_8$ stands for the same or different organo groups derived from previously defined reactants.

The molecular weight, viscosity, phosphorus content and functionality of the products of this invention may vary over wide limits. Typical product properties and composition limits are tabulated below:

| Viscosity (cps) | 600 to 60,000 |
|---|---|
| Phosphorus content (wt. %) | 13 to 23 |
| OH number | 5 to 250 |
| Acid number | 0.5 to 10 or more |

The novel poly (oxyorganophosphate/phosphonate) products represented by Formula (I) are produced by the two step process of the proceeding section with the limitation that only the organo phosphonates of Class II are reacted with phosphorus pentoxide in the first process step.

Preferred products of this invention are poly (oxyorganophosphate/phosphonate) products which are non-functional or have low hydroxyl functionality (Viz., hydroxyl numbers from 1 to 50). Especially preferred are non-functional or low hydroxyl functional poly (oxyorganophosphate/phosphonate) products according to the Formula I wherein R, $R_1$ and $R_2$ are alkyl groups of 1 to 10 carbon atoms. These alkyl substituted products contain a high percentage of phosphorus and are adaptable to a wide variety of applications.

The poly(oxyorganophosphate/phosphonate) products of this invention have general utility for imparting flame retardance to otherwise flammable materials. Typical of materials benefiting from improved flame retardance are molded, cast, or laminated articles, coatings, finishes, structural materials, elastomers, adhesives, foams, interlayers and textiles. The effective amount of flame retardant necessary for treatment of a specific material is readily determined by evaluation by one or more standardized flame tests. Generally, an article having an overall phosphorus content in excess of 0.7 weight percent will have flame retardant properties. The flame retardants of the invention may be used in combination with other flame retardant agents, antistatic agents, water repellants, and dyes, etc.

The poly(oxyorganophosphates/phosphonates) may be physically or chemically incorporated into materials to be flameproofed. Physical combination may be achieved simply by mixing or dissolving the poly(oxyorganophosphate/phosphonate) flame retardants in with other materials.

The products of this invention are generally soluble in polar solvents such as water, acetone, methanol, or ethanol and may be admixed directly into melts, suspensions, emulsions or solutions of materials optionally containing such solvents. Poly(oxyorganophosphate/phosphonate) products may also be used as essentially non-volatile impregnants for porous articles or cellulosic products such as paper, wood, plywood, particle board, cardboard and like materials.

A preferred aspect of this invention is the prepation of flame retardant polyurethane plastics and foams from chemical combination of hydroxyl-bearing poly(oxyorganophosphate/phosphonate) flame retardants with isocyanates. The hydroxyl number of the poly(oxyorganophosphate/phosphonate) is adjusted by the mode of preparation as hereinbefore described. For the preparation of flexible polyurethane foams it is particularly preferred to employ a low hydroxyl number poly(oxyorganophosphate/phosphonate) flame retardant based on a first step reaction product formed from a diorgano organophosphonate having alkoxy groups of at least two carbon atoms, for example, diethyl methylphosphonate or diethyl ethylphosphonate. Such flame retardants are particularly well adapted to polyurethane systems employing amine catalysts. Flexible polyurethane plastics or forms require low hydroxyl numbers of 1 to 50. Rigid plastics or foams require high hydroxyl numbers in the range of 300 to 800.

Polyurethane compositions employing the poly(oxyorganophosphate/phosphonate) of this invention as polyol reactants are prepared by conventional polyurethane formation techniques such as the quasi-prepolymer, prepolymer, and one-shot techniques.

Any conventional isocyanate reactant useful for polyurethane reaction may be used in combination with the polyols of this invention. Organic isocyanate reactants are exemplified by 2,4- and 2,6-toluene diisocyanate, hexamethylene diisocyanate, and xylylene diisocyanate. Dimers and trimers of isocyanates as well as mixtures of isocyanates may be used.

In the preparation of polyurethanes, other polyols may be used with the hydroxyl-bearing poly(oxyorganophosphates/phosphonates) of this invention. Illustrative of other polyols are ethylene glycol, propylene glycol, glycerol, pentaerythritol, polyethylene glycols, trialkanolamines, sorbitol, and oxypropylated glycerol.

Another aspect of this invention is the use of poly(oxyorganophosphate/phosphonate) products for imparting flame retardance to textiles.

The word "textiles" includes woven, knitted and non-woven fabrics. The poly(oxyorganophosphate/phosphonate) products of this invention are bound to the textile by incorporation in an adherent resin binder. A preferred flame retarded textile contains resin derived from hydroxyl reactive materials such as isocyanates or aminoplasts in combination with hydroxyl-bearing poly(oxyorganophosphate/phosphonate). Suitable isocyanates have been described. Examples of aminoplasts are methylated methylolamino triazines, urea-glyoxal condensation products, and urea-glyoxal-formaldehyde condensation products.

Textiles suitable for treatment include cotton, wool, rayon, glass fiber, acrylics, polyester, cotton/polyester blends, acrylonitrile, vinylidene chloride and blends of such materials.

The poly(oxyorganophosphate/phosphonate) products of this invention may be applied to the textiles as a melt, solution, suspension, or emulsion by conventional means such as padding, dipping or spraying.

Carpeting and upholstery are advantageously back-coated with compositions containing a binder and a flame retardant effective amount of poly(oxyorganophosphate/phosphonate) products of this invention.

The effective concentration of flame retardant on the fabric may be determined by routine experimentation using standard textile flame retardancy tests as criteria.

The following Examples illustrate the practice of this invention: (All percentages are by weight unless otherwise indicated).

EXAMPLE I

In a 12 liter, 3-neck glass reaction flask 2710 grams of DMMP (21.85 moles) was gradually reacted with stirring at 25°–80° with 2710 grams of $P_2O_5$ (19.08 moles). After an extra hour at 80°–90°, this metaphosphate phosphonate was treated at 50°–60° with 620.4 grams of ethylene glycol (10 moles). Trimethyl phosphite (1 g) was added to remove color. After an extra hour at 70°–80°, ethylene oxide was passed in at 50°–60° for approximately 15 hours. 41 g of stannous octoate were added and addition of ethylene oxide was continued to acid number 3.4. Yield was 9149 grams. Hydroxyl number was 129. The product contained 20% Phosphorus.

EXAMPLE II

An aqueous pad bath was prepared using 32% by weight (total composition) of the polyethylene methylphosphate/phosphonate of Example I, 6% (dry basis) of a methylolated melamine resin, 0.17% (dry basis) of zinc nitrate, and 0.01% of a common surfactant. Samples of 6.3 ounce/yd.$^2$ (214 gm/m$^2$) cotton tenting fabric were padded in this solution. After drying at 121° C., the fabric was cured 1½ minutes in a 149° C. oven, and rinsed with hot water to give a final 29.2% add-on (conditioned to 21° C.). In a second treatment, the flame retarded fabric was padded in an aqueous bath consisting of 1.2% of a polymeric fluorocarbon water repellent, 1% of a methylolated melamine-stearamide water repellent, and 0.066% (dry basis) of zinc nitrate. The fabrics were again dried, followed by one minute curing in a 149° C. oven. Equilibrated to 65% Rel. humidity at 21° C. and ignited in the standard CPAI-84 flame retardancy test, a 14.2 cm. char length was observed. After a 72 hour leach with water, another strip exhibited a char length of 15.2 cm. A 16.5 cm. char length is acceptable.

EXAMPLE III

Dimethyl methylphosphonate (677.5 grams, 5.46 moles) was gradually reacted at 25°–80° with portions totalling 677.5 g of phosphorus pentoxide (4.77 moles). After an additional hour at 87°, this metaphosphonate/methyl phosphonate was slowly treated at 50°–55° with 155 grams of ethylene glycol (2.5 moles). Trimethyl phosphite (1 cc) was added to minimize color. Introduction of ethylene oxide gas at 60°–65° during about 15 hours produced 2290 grams of product with an acid number of 13.2, a hydroxy number of 130, and phosphorus content of 20.3%.

EXAMPLE IV

An aqueous pad bath was prepared, containing 30% (of total bath weight) neat flame retardant of Example III, 7% (dry basis) of a common methylolmelamine resin, 0.33% (dry basis) of zinc nitrate, and 0.5% of a fatty alcohol-based antimigrant surfactant. Carbon black and two pigments, plus 0.09% $NH_3$ contributed another 2.24% to the bath. A cotton tenting cloth was padded in this solution. Dried at 121° C., and cured 1½ minutes in a 149° C. oven, it was then washed in hot water and dried to equilibrium at 65% rel. humidity and 21° C. The total add-on was 25.3%. For water repellency, this cloth was then padded in an aqueous bath containing 1.2% of a polymeric fluorocarbon, and 1% of a methylolated melamine-stearamide water repellents, plus 0.067% (dry basis) of zinc nitrate. The cloth was dried, and cured a second time at 149° C. for 1 minute. After the 72 hour washing-leaching, (dried to equilibrium with 65% relative humidity, 21° C.) a strip was ignited for the CPAI-84 (Canvas Products Association International—12 second ignition) standard flame retardancy test. A char length of 14.7 cm. was obtained.

EXAMPLE V

Three kilos of dimethyl methylphosphonate (24.2 moles) was reacted in portions with 3 kilos of $P_2O_5$ (21.1 moles) and heated an extra hour at 97°–99°. Ethylene glycol (678 g., 11.1 moles) was slowly added at 56°–60°, and kept another hour 56°–60°. Ethylene oxide was introduced at 57°. When nearly finished, this step was catalyzed by addition of 50 g stannous octoate. Further oxyethylation at 100° reduced acid number to 1.4. Yield of product was 10720 grams, 19.9% P, OH number 126. The product had a hydroxyl number of 126 and a phosphorus content of 19.9 weight percent.

EXAMPLE VI

An aqueous pad bath was prepared containing 32 percent neat flame retardant of Example V, 6% (dry basis) of methylolmelamine resin, 0.17% (dry basis) zinc nitrate, 0.25% of a fatty alcohol-derived anti-migrant surfactant, and 2.24% of mixed pigments and ammonia. A piece of 6.3 ounce/yd.$^2$ (213.57 gm/m$^2$) cotton drill fabric was padded in this solution to attain 29.6% add-on. The sample was equilibrated to 65% relative humidity and 21° C. Char length (by CPAI-84 test) was 13.7 cm. After a second padding (H$_2$O repellent), the fabric was dried, and cured 1 minute at 149° C., then leached 72 hours with water. The char length was then 14.22 cm. In another experiment with the product of Example 4, the second padding was eliminated entirely by substitution of 2.4% of a different fluorocarbon water repellent to the first pad bath. The hot water rinse, drying and cure were performed as above. After the 72 hour leach, the char length was again 14.2 cm. (16.5 cm. passes the test).

EXAMPLE VII

An aqueous pad bath was prepared using 25% neat flame retardant of Example I, 8% (dry basis) of a common methylolmelamine resin, 0.5% sodium bisulfate, and 0.8% softener. A 4.4 ounce/yd$^2$ (149 gm/m$^2$) sample of polyester/cotton (12%/88%) was padded in the solution and processed by curing and rinsing to a 33% add-on, (the sample retained 85% of the total cured residue during rinse). The vertical char after 50 detergent washes was 17.4 cm.

EXAMPLE VIII

Preparation of Poly(Ethylene Methyl Phosphate/Methylphosphonate) Based on Oxyethylated Tetrabromobisphenol A:

Methyl metaphosphate/methylphosphonate was prepared as described in Example I from equal weights of DMMP and P$_2$O$_5$. Then 660 grams of this anhydride, containing 2.66 moles of methylphosphonate and 4.65 moles of phosphate type phosphorus was warmed with portions of oxyethylated tetrabromobisphenol A at 60°–70°. A total of 569 grams (0.9 mole) of this diol was used. During the addition, simultaneous addition of ethylene oxide aided in reducing the high viscosity of this mixture. Eight grams of stannous octoate catalyst was thereafter added, and neutralization with ethylene oxide finished at 100°. The 1623 grams of product was diluted with 67 grams isopropanol. Product analysis disclosed 13.4% phosphorus and 17.1% bromine.

EXAMPLE IX

An aqueous pad bath was prepared, using as flame retardant the flame retardant of Example VIII. The pad bath composition contained 25% flame retardant, 10% methylolmelamine resin (dry basis), 0.33% zinc nitrate catalyst (dry basis), and 0.1% penetrant surfactant. A piece of 3.7 ounce/yd$^2$ (125 gm/m$^2$) 50/50 polyester/cotton sheeting was padded in the solution, dried at 121° C., and cured 3 minutes at 166° C. to a 40.8% add-on. After customary hot water wash, the DOC-FF3-71 (Department of Commerce Flammable Fabrics test method) flammability test* yielded a 6.9 cm. char. Another cloth sample with a 43.6% cured add-on had a 16 cm. char after 50 detergent washes.

*The DOC FF3-71 standard employs 3 minute ignition of a vertical 25.4 cm. bone-dry strip.

EXAMPLE X

Poly(Ethylene Methylphosphate/methylphosphonate) containing dibromopropyl ester groups:

Dimethyl methylphosphonate (248 grams, 2 moles) was reacted portionwise at 30°–60° with 285 g of phosphorus pentoxide (2 moles). The resulting metaphosphate/was further heated at 92° for one hour, then briefly to 120°. Cooled to 75°, it was treated dropwise slowly with 217 grams of dibromopropanol (1 mole), with another extra hour of heating at 80°–90°. Ethylene oxide gas was introduced at 95°–100°. When the acid number in methanol had been reduced to 40, the product was treated at 50° dropwise with 24 cc of conc. HCL to remove one mole of methyl ester groups. After 3 hours at 50°–80°/20 mm, the methanolic acid number had been increased to 105. Neutralization with ethylene oxide reduced methanolic acid number to 0.8 mg KOH/gram. Yield of product was 1145 grams, having a calculated 16.2% P, and 14% Br. The hydroxyl number was increased by the acid hydrolysis step to over 170 mg KOH/gram.

EXAMPLE XI

A pad bath was prepared using the following ingredients: 59.4 gms. water, 0.1 gram of a 10% (aqueous) solution of nonionic wetting agent, 21 grams of compound prepared in EXAMPLE X, 17.5 grams of an 80% (aqueous) solution of methylolmelamine resin and 2 grams of a 25% (aqueous) solution of zinc nitrate. A piece of 3.7 oz./yd$^2$ (125 gm/m$^2$) cotton flannel was padded in this solution, dried at 121° F., and cured one minute at 177° C. After a hot water rinse step, the dried add-on was 23.8%. After 50 washes, the add-on was 23.8%. After 50 detergent washes, the add-on was 14.1%, representing 59–60% retention. In the standard FF3-71 test for flame retardancy, a char length of 8.3 cm. was obtained.

EXAMPLE XII

Five hundred grams of the dibromopropyl polyethylene phosph(on)ate of Example X was heated to 50° and treated with 13 grams additional conc. HCL. After two hours at 80° and subatmospheric pressure, the product was reneutralized at 80°–100° with ethylene oxide, catalyzed by 0.5% stannous octoate. The yield was 552 grams with acid number 1.0. Product analysis was 14.6% phosphorus and 12.6 percent bromine.

EXAMPLE XIII

An aqueous pad bath was prepared, using 31.5% of the product of Example XII, 0.01% (dry basis) nonionic penetrant, 0.75% (dry basis) zinc nitrate, and 21% (dry basis) methylolmelamine resin. A sample of 50/50 polyester/cotton cloth was padded in this solution to a 73% wet pickup, dried and cured 3 minutes at 177° C. After a hot water rinse and drying, a 26% add-on was obtained. In the standard FF3-71 flame retardancy test, an 8.3 cm. char was obtained.

EXAMPLE XIV

Dimethyl methylphosphonate (745 grams, 6 moles) was reacted portionwise with 709 grams of phosphorus pentoxide (7.21 moles). After an extra hour at 85°, a part of this (433.8 grams) was treated at 70°–80° with portions of 283 grams of dibromoneopentylene glycol during ¾ hour. After an extra hour at 80°–83°, ethylene oxide was introduced at under 80° until the end, when the product was briefly heated to 100° with ethylene oxide. The yield of product was 983 grams (corresponding to about 1.29 moles epoxide per phosphorus atom). Acid number of the product was 13.4. Products analysis disclosed 15 percent phosphorus and 17.5 percent bromine.

EXAMPLE XV

Use of Dibromoneopentylene Glycol-based Product on Polyester/Cotton Blend:

An aqueous pad bath was prepared containing 25% of the bromine-containing product of Example XIV, 20% (dry basis) of a common methylolmelamine resin, 0.01% of a nonionic penetrant, 1% of a polyethylene fabric softener (dry basis), and 1.0% (dry basis) of zinc nitrate. A piece of 50/50 polyester/cotton blend fabric was padded in the solution to a 75% wet pickup, dried (121° C.), and cured 3 minutes in a 177° C. oven. After a standard hot water rinse, the dried add-on was 20.6%. In the FR test FF3-71, a char length of 5.08 cm. was obtained.

EXAMPLE XVI

Preparation of Poly(Ethylene Methylphosphate/Methylphosphonate) Based on Methanol:

Dimethyl Methylphosphonate (659 grams, 5.3 moles) was treated portionwise at 25°–70° with 628 grams of $P_2O_5$ (4.42 moles). After an extra hour and a half at 79° C., this anhydride was treated slowly at 65° C. with 74.2 g of methanol (2.32 moles). After an extra hour at 70° C., this was treated with a stream of ethylene oxide at 37°–60° C. The oxyethylation was effected at 100° toward the conclusion of the reaction. Finally, 10 grams of stannous octoate was added and the neutralization continued to acid number 5.5. The product weighed 1986 grams, an uptake of 14.5 moles of ethylene oxide. Analysis: 20.5% P, hydroxyl number 61.

EXAMPLE XVII

An aqueous pad bath was prepared containing 21% of the product of Example XVI, 14% (dry basis) of methylolated melamine resin, 0.5% (dry basis) of zinc nitrate, 0.01% (dry basis) of anionic penetrant, and 1% (dry basis) polyethylene softener. A sample of 4 oz/yd$^2$ (135.6 gm/m$^2$) cotton flannel was padded in this bath, dried (121° C.), and cured 1 minute in a 177° C. oven. After a hot water rinse, the dried cloth exhibited a 20.7% add-on. After 50 detergent washes, the add-on was reduced to 14.5%, and yielded char lengths of 3.8 cm. and 4.4 cm.

EXAMPLE XVIII

Poly(Ethylene Methyl Phosphate/Methylphosphonate) based on Pentaerythritol:

962.8 grams (10.6 gram atoms phosphorus) of the first step metaphosphate.phosphonate of Example XIV was treated slowly at 70°–120° with 204 grams of pentaerythritol (1.5 moles). Trimethylphosphonate (1 cc) was added to reduce color. Ethylene oxide was introduced at 70°–100° C. Later, 5.6 grams stannous octoate was added. Oxyethylation was followed by nitrogen sparging. Addition of 15 grams of a common diepoxide stabilizer yielded 1827 grams of a product with 17.7% P, acid number 4.0, and a hydroxyl number of 220.

EXAMPLE XIX

A pad bath was prepared with 21% of the polymer of Example XVIII, 14% (dry basis) of methylolmelamine resin and the other addends (Zn)NO$_3$)$_2$, softener penetrant). Cotton flannel padded, dried and cured as above, was hot-water rinsed and dried. Retention of the flame retardant was 65%. After 50 detergent washes, overall retention was 40.8, and the DOC FF3-71 char length was 13 cm.

EXAMPLE XX

Ten moles (1240 grams) of dimethyl methylphosphonate was treated with 3⅓ moles (473 grams) of phosphorus pentoxide and reacted at 80° C. for one hour. The reaction mixture was then treated with ethylene oxide at 60° C. to 100° C. The acid number (HCl method) of the product was 8.2.

Unreacted dimethyl methylphosphonate (280 grams) was stripped out of the reaction product to give a dimethyl methylphosphonate to phosphorus pentoxide ratio of 2.32. Ethylene glycol (6.7 grams) was added to the reaction mixture followed by introduction of ethylene oxide. The final product had an acid number of 3.5, a viscosity of 650 cps., a hydroxyl number of 12.2 and a phosphorus content of 21.9 percent.

EXAMPLE XXI

A flexible polyurethane foam was prepared from the following recipe:

| (All proportions are parts by weight) | |
|---|---|
| Product of Example XX | 5 pts. |
| Niax 1646 Polyol (a polyether polyol, M.W. 4600) | 100 pts. |
| Surfactant LS 5720 (non-ionic non-hydrolyzable silicone) | 1 pts. |
| Water | 4 pts. |
| Dabco 33LV (diazabicyclooctane) | 0.3 pts. |
| Niax ESN (N-ethylmorpholine) | 0.23 pts. |
| Stannous octoate | 0.4 pts. |
| Dupont TDI 80/20 (toluene diisocyanate) | 50.5 pts. |

The above ingredients were mixed at room temperature and the resultant foam tested for flammability by the Federal Motor Vehicle Safety Standard 302 Test and the State of California (Department of Consumer Affairs, Bureau of Home Furnishings, Technical Information Bull. No. 117) Vertical Test. The Sample prepared according to this Example passed both tests.

EXAMPLE XXII

This Example illustrates backcoating of upholstery fabric with backcoating compositions containing poly-(oxyorganophosphates/phosphonates) of this invention. A backcoating formulation of the following compositions was prepared:

| Ingredient | Parts by Weight |
|---|---|
| Rhoplex HA-8 (Acrylic resin copolymer emulsion) | 67 |
| Water | 8.5 |
| Paragum 109 (polycarboxylated acrylate) | 1.35 |
| NH$_4$OH | 1.5 |
| Poly (oxyorganophosphate/phosphonate) of Example I | 15 |
| Aerotex M-3 (methylated methylolamino-triazine) | 5 |

| -continued | |
|---|---|
| Catalyst X-4 25% Zn(NO$_3$)$_2$ | 3 |
| pH | 6.0 |
| Viscosity - Brookfield RVT | 36,000 cps. |
| Cure Time | 7 min. at 163° C. |
| Color | No Change |
| Test Fabric: | |
| Cotton Corduroy 12.8 oz/yd.$^2$ (434 gms/m$^2$) | 2 |

| | Before Treatment | After Treatment |
|---|---|---|
| Fabric Classification Procedure: | D | B |

The above backcoating formulation was applied uniformly to one side of the test fabric with a spatula to an add-on level of 47.7 weight percent (dry basis). The sample was evaluated by the U.S. Department of Commerce Provisional FF 6-77 test. Cigarette radius of burn classifications of "C" and "D" are unacceptable. An acceptable test rating of "B" was achieved by the back-coated fabric prepared by this Example.

According to the provisions of the Patent Statutes, there are described above the invention and what are now considered to be its best embodiments. However, within the scope of the appended claims, it is to be understood that the invention may be practiced otherwise than specifically described.

What is claimed:

1. A process for preparing poly(oxyorganophosphate/phosphonate) flame retardant product represented as repeating units having the average formula:

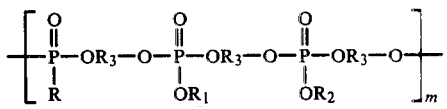

wherein m is an integer from 1 to 50; R, R$_1$, and R$_2$ are the same or different radicals selected from saturated hydrocarbon radical, alkaryl radical, aralkyl radical, and aryl radical; and R$_3$ is:

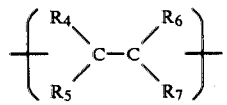

wherein R$_4$, R$_5$, R$_6$, and R$_7$ are the same or different radicals selected from hydrogen atom, alkaryl radical, aralkyl radical, aryl radical, saturated hydrocarbon radical, and halogenated hydrocarbon radical; by a two step sequential reaction which comprises:

(1) reacting diorgano organophosphonate represented by the formula:

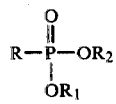

wherein R, R$_1$, and R$_2$ are the same or different organic radicals selected from saturated hydrocarbon radical, alkaryl radical, aralkyl radical, and aryl radical; with reactant consisting of (i) phosphorus oxide reagent, or (ii) phosphorus oxide reagent with an alcohol, to yield a metaphosphate/phosphonate reaction product, wherein the mole ratio of said diorgano organophosphonate to said phosphorus oxide reagent (as P$_2$O$_5$) is in the range from about 1:1 to about 2.5:1, and said optionally employed alcohol is not in excess of one mole of alcohol hydroxyl per three moles of phosphorus anhydride unit formed by the reaction of phosphorus oxide reactant with diorgano organophosphonate, and;

(2) reacting the reaction product of step (1) with reactant comprising (I) epoxide, or (II) epoxide with an alcohol to yield poly(oxyorganophosphate/phosphonate) product.

2. The process of claim 1 wherein R, R$_1$ and R$_2$ are selected from alkyl radicals of one to ten carbon atoms.

3. The process of claim 1 wherein the diorgano organophosphonate of step (1) is selected from the group consisting of dimethyl methyl phosphonate, diethyl methylphosphonate, dimethyl ethylphosphonate, diethyl ethylphosphonate and diethyl phenylphosphonate.

4. The process of claim 1 wherein the epoxide of step (1) is represented by the formula:

wherein R$_4$, R$_5$, R$_6$ and R$_7$ may be the same or different radicals selected from hydrogen atom, alkyl radical, aryl radical or haloalkyl radical.

5. The process of claim 1 wherein the epoxide of step (2) is selected from the group consisting of ethylene oxide, 1,2-epoxypropane, epoxybutane, epoxyhexane, epichlorohydrin, epibromohydrin, or styrene oxide.

6. The process of claim 1 wherein the phosphorus oxide reagent consists essentially of phosphorus pentoxide.

7. The process of claim 1 wherein epoxide is used in step (2) in proportions of from about 0.8 to about 1.3 moles per gram atom of phosphorus in the metaphosphate/phosphonate reaction product of step (1).

8. The process of claim 1 wherein step (1) is carried out between the limits of about 0° C. to about 200° C. and step (2) is carried out between the limits of about 0° C. to about 180° C.

9. The process of claim 1 wherein a catalytically effective amount of Lewis acid or Lewis base is used in step (2).

10. The process of claim 1 wherein alcohol used in step (1) or step (2) may be the same or different and is selected from classes of alcohols consisting of: primary alcohols, secondary alcohols, tertiary alcohols, phenols, aromatic alcohols, polyhydric alcohols, alcohol acids, alcohol esters, alcohol amides, alcohol ethers, sulfur-containing alcohols, phosphorus-containing alcohols, oxy(halo)phenols, or mixtures of said classes of alcohols.

11. The product formed from the process of claim 1.

12. The product formed from the process of claim 2.

13. The product formed from the process of claim 3.

14. A process for preparing poly(oxyorganophosphate/phosphonate) product by a two step reaction which comprises:

(1) reacting diorgano organophosphonate with reactant comprising (i) phosphorus oxide reagent, or (ii) phosphorus oxide reagent with an alcohol to yield a metaphosphate/phosphonate reaction product; wherein the mole ratio of said diorgano organophosphonate to said phosphorus oxide reagent (as $P_2O_5$) is in the range from about 1:1 to about 2.5:1, and said optionally employed alcohol is not in excess of one mole of alcohol hydroxyl per three moles of phosphorus anhydride unit formed by the reaction of phosphorus oxide reactant with diorgano organophosphonate, and thereafter;

(2) reacting the reaction product of step (1) with reactant comprising (I) strained-ring oxygen heterocycle reactant, or (ii) strained-ring oxygen heterocycle reactant and an alcohol to yield poly(oxyorganophosphate/phosphonate) product.

15. A process for preparing poly(oxyorganophosphate/phosphonate) flame retardant product by a two step sequential reaction which comprises:

(1) reacting diorgano organophosphonate represented by the formula:

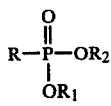

wherein R, $R_1$, and $R_2$ are the same or different organic radicals selected from alkylene radical, halogenated hydrocarbon radical, organophosphorus radical, organonitrogen radical, saturated hydrocarbon radical, alkaryl radical, aralkyl radical, and aryl radical; with reactant consisting essentially of (i) phosphorus oxide reagent, or (ii) phosphorus oxide reagent with an alcohol, to yield metaphosphate/phosphonate reaction product; wherein the mole ratio of said diorgano organophosphonate to said phosphorus oxide reagent (as $P_2O_5$) is in the range from about 1:1 to about 2.5:1, and said optionally employed alcohol is not in excess of one mole of alcohol hydroxyl per three moles of phosphorus anhydride unit formed by the reaction of phosphorus oxide reactant with diorgano organophosphonate, and (2) reacting the reaction product of step (1) with reactant comprising (I) epoxide, or (II) epoxide with an alcohol to yield poly(oxyorganophosphate/phosphonate) product.

16. The process of claim 15 wherein epoxide is used in step (2) in proportions of from about 0.8 to about 1.3 moles per gram atom of phosphorus in the metaphosphate/phosphonate reaction product of step (1).

17. The process of claim 15 wherein step (1) is carried out between the limits of about 0° C. to about 200° C. and step (2) is carried out between the limits of about 0° C. to about 180° C.

18. The process of claim 15 wherein a catalytically effective amount of Lewis acid or Lewis base is used in step (2).

19. The process of claim 15 wherein alcohol used in step (1) or step (2) may be the same or different and is selected from classes of alcohols consisting of: primary alcohols, secondary alcohols, tertiary alcohols, phenols, aromatic alcohols, polyhydric alcohols, alcohol acids, alcohol esters, alcohol amides, alcohol ethers, sulfur-containing alcohols, phosphorus-containing alcohols, halogenated alcohols, oxyorgano (halo) phenols, or mixtures of said classes of alcohols.

* * * * *

UNITED STATES PATENT AND TRADEMARK OFFICE
CERTIFICATE OF CORRECTION

PATENT NO. : 4,199,534
DATED : April 22, 1980
INVENTOR(S) : Ralph B. Fearing

It is certified that error appears in the above-identified patent and that said Letters Patent are hereby corrected as shown below:

Column 6, line 40, change "acidify" to -- acidity -- .

Column 7, line 28, change "$OR_2$" to -- $OR_2$ -- .

Column 12, line 32, change "121°F." to -- 121°C. -- .

Signed and Sealed this

Ninth Day of September 1980

[SEAL]

Attest:

SIDNEY A. DIAMOND

Attesting Officer     Commissioner of Patents and Trademarks